United States Patent [19]
Dickore et al.

[11] 3,978,068
[45] Aug. 31, 1976

[54] AZOMETHINE COMPOUNDS OF 4-AMINO-5-H-1,2,4-TRIAZIN-5-ONES AND HERBICIDAL COMPOSITIONS CONTAINING THEM

[75] Inventors: Karlfried Dickore, Leverkusen; Wilfried Draber; Helmut Timmler, both of Wuppertal; Ludwig Eue; Robert R. Schmidt, both of Cologne, all of Germany

[73] Assignee: Bayer Aktiengesellschaft, Leverkusen, Germany

[22] Filed: July 24, 1973

[21] Appl. No.: 382,243

[30] Foreign Application Priority Data
Aug. 3, 1972   Germany............................ 2238206

[52] U.S. Cl.............................. 260/240 G; 71/93; 260/248 AS; 260/249.5
[51] Int. Cl.²........................................ C07D 251/42
[58] Field of Search........ 260/240 G, 249.5, 248 AS

[56] References Cited
UNITED STATES PATENTS

| | | | |
|---|---|---|---|
| 3,671,523 | 6/1972 | Westphal et al............. | 260/248 AS |
| 3,759,910 | 9/1973 | Dickore et al............. | 260/240 G X |
| 3,847,914 | 11/1974 | Dickore et al............... | 260/248 AS |

FOREIGN PATENTS OR APPLICATIONS 44-315   9/1969   Japan............................ 260/240 G OTHER PUBLICATIONS
Zauer et al., *Periodica Polytechnic Hung.* vol. 12, pp. 259 to 275 (1968).

*Primary Examiner*—John D. Randolph
*Attorney, Agent, or Firm*—Burgess, Dinklage & Sprung

[57] ABSTRACT

Azomethine compounds of 4-amino-5-H-1,2,4-triazin-5-ones of the formula

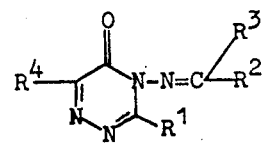

wherein:
 $R^1$ is alkyl, cycloalkyl or phenyl;
 $R^2$ is hydrogen or alkyl;
 $R^3$ is alkyl, alkoxy, cycloalkyl, cycloalkenyl, aralkyl, aryl or heteroaryl, or dialkylamino;
 $R^2$ and $R^3$ jointly can be an alkylene bridge, optionally interrupted by a hetero atom; and
 $R^4$ is alkyl or optionally substituted phenyl, are markedly effective herbicides, particularly selective herbicides for weeds growing in oats, wheat, cotton, maize, tomatoe, potatoe, soybean, and especially in beet cultivations.

26 Claims, No Drawings

AZOMETHINE COMPOUNDS OF 4-AMINO-5-H-1,2,4-TRIAZIN-5-ONES AND HERBICIDAL COMPOSITIONS CONTAINING THEM

This invention relates to certain new azomethine compounds of 4-amino-5-H-1,2,4-triazin-5-ones, to herbicidal compositions containing them and to their use as herbicides.

It is known that 3-methylthio-4-furfurylideneamino-5-H-6-isopropyl-1,2,4-triazin-5-one can be used as a herbicide from Japanese Pat. No. 547,317. However, the activity of this material is not always satisfactory, especially if low amounts and concentrations are used. It has furthermore been disclosed that 3-methylthio-4-amino-5-H-6-phenyl-1,2,4-triazin-5-one possesses herbicidal properties in German Offenlegungsschrift (German Published Specification) No. 1,542,873. However, this compound is not tolerated by beet plants. It is furthermore known that 3-methoxycarbonylamino-phenyl-N-(3'-methylphenyl)-carbamate can be used as a selective herbicide, from German Offenlegungsschrift (German Published Specification) No. 1,110,465. However, the activity of this compound, which is especially suitable for use as a beet herbicide, also leaves something to be desired if low amounts and concentrations are used.

The present invention provides azomethines of 4-amino-5-H-1,2,4-triazin-5ones of the general formula

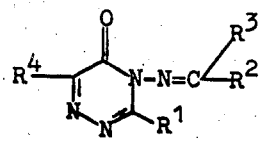
(I)

in which:
$R^1$ is alkyl of up to 20 carbon atoms, cycloalkyl or phenyl,
$R^2$ is hydrogen or alkyl of up to 4 carbon atoms,
$R^3$ is alkyl or alkoxy of up to 4 carbon atoms, cycloalkyl, cycloalkenyl, aralkyl, optionally substituted aryl or heteroaryl, or $R^3$ is dialkylamino wherein each alkyl moiety, independently of the other, contains 1 to 4 carbon atoms or the two alkyl moieties jointly represent an alkylene bridge with 2 to 6 carbon atoms which forms, with inclusion of the nitrogen atom, a heterocyclic ring which can optionally contain oxygen, sulfur or the NH group, or
$R^2$ and $R^3$ jointly represent an alkylene bridge which can be interrupted by a hetero-atom, and
$R^4$ represents alkyl with up to 4 carbon atoms or optionally substituted phenyl.

$R^1$ preferably is straight-chain or branched alkyl of 1 to 15 carbon atoms, especially of 1 to 13 carbon atoms, cycloalkyl of 3 to 6 carbon atoms or phenyl. $R^4$ is straight-chain or branched alkyl with 1 to 4 carbon atoms, especially tertiary butyl, or phenyl which can be substituted once or twice by halogen, especially chlorine, straight-chain or branched alkyl with 1 to 4 carbon atoms, halomethyl with 1 to 3 halogen atoms (especially with chlorine or fluorine, for example trifluoromethyl), alkoxy or alkylthio with 1 to 4 carbon atoms, sulphonylalkyl, especially sulphonylmethyl, or the nitro group. $R^2$ represents hydrogen or straight-chain or branched alkyl with 1 to 4 carbon atoms. $R^3$ represents straight-chain or branched alkyl or alkoxy with 1 to 4 carbon atoms, cycloalkyl or cycloalkenyl with 5 to 7 carbon atoms, aralkyl with 6 to 10 carbon atoms in the aryl moiety and 1 or 2 carbon atoms in the alkyl moiety, optionally substituted aryl with 6 to 10 carbon atoms or heteroaryl with 5 to 7 carbon atoms, especially furyl, thienyl or pyrryl; or $R^3$ represents dialkylamino wherein the alkyl moieties independently of each other contain 1 to 4 carbon atoms and can be straight-chain or branched or conjointly with the nitrogen can form a heterocyclic ring with 2 to 5 carbon atoms which can contain oxygen or sulfur, or an NH group; possible substituents of the aryl radical are: alkyl with up to 3 carbon atoms, halogen, especially chlorine, nitro and haloalkyl, especially trifluoromethyl. The aryl radical can have one or more substituents. Alternatively, $R^2$ and $R^3$ jointly preferably represent an alkylene bridge with 2 to 6 methylene members which can be interrupted by a hetero atom such as oxygen, sulfur or an NH group.

The invention also provides a process for the production of an azomethine of the formula (I) in which a 4-amino-5-H-1,2,4-triazin-5-one of the general formula

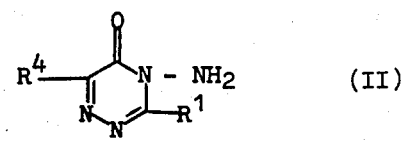
(II)

in which:
$R^1$ and $R^4$ have the above-mentioned meanings, is reacted with the aldehyde or ketone or its acetal or ketal of the general formula

(III)

in which:
$R^2$ and $R^3$ have the above-mentioned meanings and
$R^5$ represents oxygen or the $-(OR^6)_2$ group,
wherein:
$R^6$ represents alkyl with 1 to 4 carbon atoms, optionally in the presence of an acid catalyst and optionally in the presence of a diluent.

Surprisingly, the azomethines of the 4-amino-5-H-1,2,4-triazin-5-ones according to the invention show substantially better herbicidal properties than 3-methylthio-4-furfurylideneamino-5-H-6-isopropyl-1,2,4-triazin-5-one known from the state of the art and 3-methylthio-4-amino-5-H-6-phenyl-1,2,4-triazin-5-one, also known from the state of the art, which are chemically the nearest active compounds of the same type of action. Above all, however, the active compounds according to the invention appear to be substantially more suitable then previously known compounds for the selective combating of weeds in oats, wheat, cotton, maize and especially in beet. They are just as well tolerated by beet as the selective beet herbicide 3-methoxycarbonylamino-phenyl-N-(3'-methylphenyl)-carbamate known from the art but surpass the latter in respect of the general herbicidal power. The compounds which can be used according to the invention thus represent a valuable enrichment of the art.

If 3-ethyl-4-amino-6-phenyl-1,2,4-triazin-5-one and dimethylformamide-dimethylacetal are used as starting substances, the course of the reaction can be represented by the following formula scheme:

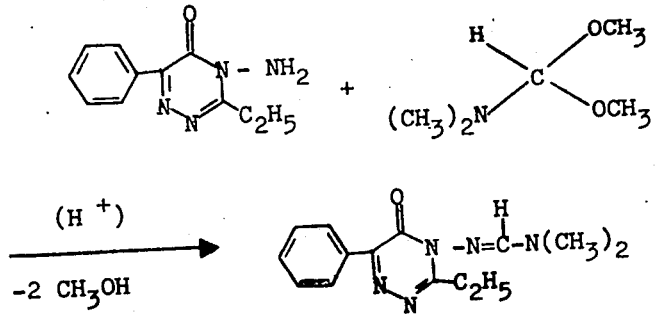

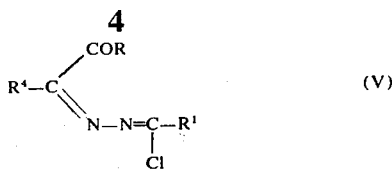

in which:
R⁴ and R¹ have the above-mentioned meanings and
R represents chlorine or alkoxy of from 1 to 4 carbon atoms are reacted with hydrazine, in the presence of an acid-binding agent and optionally in the presence of a solvent, at temperatures from 50° to 120°C.

The formula (III) provides a general definition of the aldehydes or ketones, their acetals and ketals, which are used as starting substances.

In detail, the following may be mentioned as examples of the starting substances of the formula (III): cyclohex-3-enyl-aldehyde, dimethylformamide-acetal, acetone, benzaldehyde, 4-nitrobenzaldehyde, 4-methylbenzaldehyde, acetophenone, formic acid ethyl ester, cyclohexanone, cyclohex-3en-1-one, 2-furylaldehyde, 2-furyl methyl ketone, 2-thienylaldehyde, and 2-pyrriylaldehyde.

The aldehydes, ketones, their acetals and their ketals, which can be used in the process according to the invention, are known.

Possible diluents in the reaction according to the invention include all inert organic solvents. Preferred examples include hydrocarbons such as benzene or toluene, ethers such as dioxan or tetrahydrofuran, alcohols such as ethanol, isopropanol or butanol and nitriles such as acetonitrile.

As acid catalysts it is possible to use Lewis acids such as aluminum-(III) chloride, iron-(III) chloride, copper-(II) nitrate, tin-(II) chloride; organic acids such as p-toluenesulphonic acid; and anhydrous inorganic acids such as gaseous hydrogen chloride. p-toluenesulphonic acid is particularly suitable.

The reaction temperatures can be varied over a wide range. In general the reaction is carried out at 0° to 120°C, preferably 50° to 120°C.

The reaction is in general carried out under normal pressure.

In carrying out the process according to the invention, 1 to about 2 mols of aldehyde, ketone, acetal or ketal of the formula (III) and 0.01 to about 3.5 mols of an acid catalyst are generally employed per mol of 4-amino-5-H-1,2,4-triazin-5-one of the formula (II). It is possible to exceed the stoichiometric ratios further but this does not produce any significant increase in yield.

To isolate the compounds of the formula (I), the solvent may be distilled off wholly or partially, the precipitate which may be produced may be filtered off, The formula (II) provides a general definition of the 4-amino-5-H-1,2,4-triazin-5-ones used as starting substances.

The following may be mentioned as examples of the 4-amino-5-H-1,2,4-triazin-5-ones which can be used in the process according to the invention: 3-methyl-4-amino-6-phenyl-5-H-1,2,4-triazin-5-one, 3-ethyl-4-amino-6-phenyl-5-H-1,2,4-triazin-5-one, 3-propyl-4-amino-6-phenyl-5-H-1,2,4-triazin-5-one, 3-isopropyl-4-amino-6-phenyl-5-H-1,2,4-triazin-5one, 3-methyl-4-amino-6-(3'-trifluoromethylphenyl)-5-H-1,2,4-triazin-5-one, 3-methyl-4-amino-6-(2'-chlorophenyl)-5-H-1,2,4-triazin-5-one, 3-ethyl-4-amino-6-(2'chlorophenyl)-5-H-1,2,4-triazin-5-one, 3-ethyl-4-amino-6-(4'-chlorophenyl)-5-H-1,2,4-triazin-5-one, 3-cyclopropyl-4-amino-6-phenyl-5-H-1,2,4-triazin-5-one, 3-ethyl-4-amino-6-tertiary butyl-5-H-1,2,4-triazin-5-one, 3-iso-propyl-4-amino-6-tertiary butyl-5-H-1,2,4-triazin-5-one, 3-iso-propyl-4-amino-6-(4'-methylphenyl)-5-H-1,2,4-triazin-5-one, 3-ethyl-4-amino-6-(3'-trifluoromethylphenyl)-5-H-1,2,4-triazin-5-one and 3-ethyl-4-amino-6-(4'-nitrophenyl)-5-H-1,2,4-triazin-5-one.

Some of the 4-amino-5-H-1,2,4-triazin-5-ones of the formula (II) are the subject of earlier patent applications (compare German patent applications Ser. Nos. P 21 07 757 and P 21 38 031, published on Feb. 2, 1971 and July 29, 1971, respectively. They may be obtained when (a) glyoxilic acid ester 2-acylhydrazones of the general formula

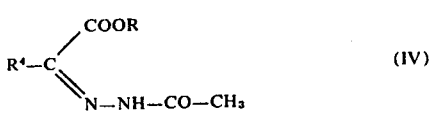

in which:
R⁴ has the above-mentioned meaning and
R represents alkyl with 1 to 4 carbon atoms are reacted with hydrazine, optionally in the presence of a basic catalyst and of a solvent, at temperatures from 50° to 150°C; or when (b) diazabutadienes of the general formula

EXAMPLE 1 — Preparation of 3-methyl-4-benzylideneamino-6-phenyl-5-H-1,2,4-triazin-5-one

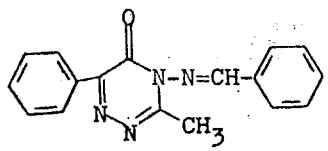

10.1 g (0.05 mol) of 3-methyl-4-amino-6-phenyl-1,2,4-triazin-5-one, 10 g (0.09 mol) of benzaldehyde, 0.3g of p-toluenesulphonic acid and 300 ml of benzene were boiled for 8 hours under a water separator. Thereafter the reaction mixture was filtered and the solvent was distilled off in vacuo. The residue solidfied after trituration with petroleum ether.

After recrystallization, 11.0 g (76% of theory) of 3-methyl-4-benzylideneamino-6-phenyl-5-H-1,2,4-triazin-5-one of melting point 179°C were obtained.

EXAMPLE 2 — Preparation of 3-ethyl-4-(3',3'-dimethylformamidino-1)-6-phenyl-5-H-1,2,4-triazin-5-one

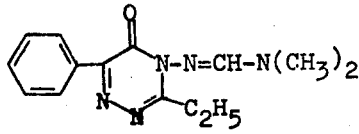

10.8 g (0.05 mol) of 3-ethyl-4-amino-6-phenyl-1,2,4-triazin-5-one were dissolved in 100 ml of alcohol and heated overnight to the boil under reflux with 7 g (0.05 mol) of dimethylformamide-dimethylacetal in the presence of 0.5 g (0.003 mol) of p-toluenesulphonic acid. The residue which remained after distilling off the ethanol in vacuo solidified to crystals.

After recrystallization from isopropanol 11 g (81% of theory) of 3-ethyl-4-(3',3'-dimethylformamidino-1)-6-phenyl-5-H-1,2,4-triazin-5-one of melting point 123°C were obtained.

3-ethyl-4-amino-6-phenyl-5-H-1,2,4-triazin-5-one, used as the starting product, was obtained as follows:

10.0 g (0.2 mol) of hydrazine hydrate, dissolved in 20 ml of dimethylformamide, were added dropwise to a solution of 26.7 g (0.1 mol) of 1-phenyl-1-ethoxycarbonyl-4-chloro-4-ethyl-2,3-diazabutadiene in 100 ml of dimethylformamide at a temperature of 5°C to 10°C, whilst stirring. After stirring for 3 hours, 250 ml of water were added to the reaction mixture. The whole was left to stand overnight. Thereafter, the solid which had precipitated was filtered off, well rinsed with water and dried. The yellowish-white crude product (17.4 g = 80% of theory) was purified by recrystallization from isopropanol/water. 14.5 g (67.1% of theory) of 3-ethyl-4-amino-6-phenyl-5-H-1,2,4-triazin-5-one of melting point 164°C were obtained.

EXAMPLE 3 — Preparation of 3-cyclohexyl-4-isopropylidene-amino-6-phenyl-5-H-1,2,4-triazin-5-one

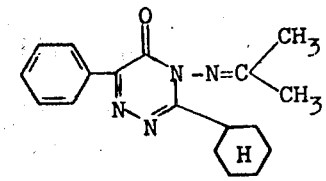

13.5 g (0.05 mol) of 3-cyclohexyl-4-amino-6-phenyl-5-H-1,2,4-triazin-5-one were dissolved in 250 ml of acetone, 0.1 g (0.0006 mol) of p-toluenesulphonic acid was added and the mixture was heated to the boil under reflux for 1 hour. The reaction solution was filtered hot, thereafter the solvent was partly distilled off, and the residue was treated with 20 to 50 ml of isopropanol. The crystalline precipitate thereby obtained was filtered off and washed with ether.

13.4 g (88% of theory) of 3-cyclohexyl-4-isopropylidene-amino-6-phenyl-5-H-1,2,4-triazin-5-one of melting point 131°–134°C were thus obtained.

3-Cyclohexyl-4-amino-6-phenyl-5-H-1,2,4-triazin-5-one used as the starting product, was prepared as follows:

28.8 g (0.1 mol) of phenylglyoxylic acid methyl ester-2-hexahydrobenzoylhydrazone and 10 g of hydrazine hydrate (0.2 mol) were stirred in 100 ml of pyridine, which had been dried over potassium hydroxide, for 45 minutes at 100°C and the mixture was subsequently cooled. Thereupon, the mixture solidifed to a paste. 100 ml of water were added and the whole was stirred for some hours and the product filtered off. After washing with water and drying, 5.3 g (19.7% of theory) of 3-cyclohexyl-4-amino-6-phenyl-5-H-1,2,4-triazin-5-one were obtained in colorless flakes of melting point 178°–180°C.

EXAMPLES 4–46

The compounds listed in the following table, Table 1, were prepared analogously.

Table 1

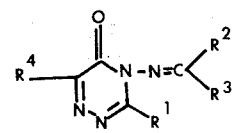

| Example No. | $R^1$ | $R^2$ | $R^3$ | $R^4$ | Melting point °C |
|---|---|---|---|---|---|
| 4 | $C_2H_5$ | $CH_3$ | $CH_3$ | $C(CH_3)_3$ | 62–63 |
| 5 | $C_2H_5$ | H | $OC_2H_5$ | $C(CH_3)_3$ | 86 |

Table 1-continued

| Example No. | R¹ | R² | R³ | R⁴ | Melting point °C |
|---|---|---|---|---|---|
| 6 | $C_2H_5$ | H | (phenyl) | $C(CH_3)_3$ | 103–105 |
| 7 | $C_2H_5$ | H | (furyl) | $C(CH_3)_3$ | 112–114 |
| 8 | $CH(CH_3)_2$ | $CH_3$ | $CH_3$ | $C(CH_3)_3$ | 89 |
| 9 | $C_2H_5$ | —$(CH_2)_5$— | | $C(CH_3)_3$ | 58–60 |
| 10 | $C_2H_5$ | $CH_3$ | $CH_3$ | $C_6H_5$ | 146 |
| 11 | $C_3H_7$ | $CH_3$ | $CH_3$ | $C_6H_5$ | 102 |
| 12 | $C_2H_5$ | H | $C_6H_5$ | $C_6H_5$ | 115–117 |
| 13 | $C_2H_5$ | H | (cyclohexenyl) | $C_6H_5$ | 124–126 |
| 14 | $C_2H_5$ | H | (o-tolyl) | $C_6H_5$ | 122 |
| 15 | $C_6H_5$ | $CH_3$ | $CH_3$ | $C_6H_5$ | 137–140 |
| 16 | $C_3H_7$-i | $CH_3$ | $CH_3$ | $C_6H_5$ | 96–99 |
| 17 | (cyclopropyl) | $CH_3$ | $CH_3$ | $C_6H_5$ | 146.5 |
| 18 | $CH_3$ | $CH_3$ | $CH_3$ | $C_6H_5$ | 99 |
| 19 | $CH_3$ | H | (cyclohexenyl) | $C_6H_5$ | 117 |
| 20 | $CH_3$ | H | $C_6H_5$ | $C_6H_5$ | 177–179 |
| 21 | $C_5H_{11}$-n | $CH_3$ | $CH_3$ | $C_6H_5$ | 82–85 |
| 22 | $C_5H_{11}$-n | H | (cyclohexenyl) | $C_6H_5$ | 62 |
| 23 | $C_5H_{11}$-n | H | $C_6H_5$ | $C_6H_5$ | 106–108 |
| 24 | $(CH_2)_2CH(CH_3)_2$ | $CH_3$ | $CH_3$ | $C_6H_5$ | 83.5 |
| 25 | $(CH_2)_2CH(CH_3)_2$ | H | $C_6H_5$ | $C_6H_5$ | 80.5 |
| 26 | $C_6H_{13}$-n | $CH_3$ | $CH_3$ | $C_6H_5$ | 78–79 |
| 27 | $C_6H_{13}$-n | H | $C_6H_5$ | $C_6H_5$ | 91–92 |
| 28 | $C_{13}H_{27}$-n | $CH_3$ | $CH_3$ | $C_6H_5$ | 77 |
| 29 | $C_4H_9$-n | $CH_3$ | $CH_3$ | $C_6H_5$ | 91 |
| 30 | $CH_3$ | H | (p-tolyl-$CH_3$) | $C_6H_5$ | 150–152 |
| 31 | $CH_3$ | H | (p-$NO_2$-phenyl) | $C_6H_5$ | 183–185 |
| 32 | $C_3$ | H | (o-Cl-phenyl) | $C_6H_5$ | 195 |
| 33 | $C_2H_5$ | $CH_3$ | $CH_3$ | $CH_3$-(phenyl) | 152 |
| 34 | $C_2H_5$ | H | $C_6H_5$ | $CH_3$-(phenyl) | 143 |

Table 1-continued

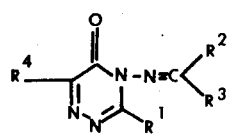

| Example No. | R¹ | R² | R³ | R⁴ | Melting point °C |
|---|---|---|---|---|---|
| 35 | CH(CH₃)₂ | CH₃ | CH₃ | CH₃-C₆H₄- | 109 |
| 36 | CH(CH₃)₂ | H | C₆H₅ | CH₃-C₆H₄- | 118 |
| 37 | C₂H₅ | H | N(CH₃)₂ | C₆H₅ | 123 |
| 38 | CH₃ | H | N(CH₃)₂ | C₆H₅ | 110 |
| 39 | C₂H₅ | CH₃ | CH₃ | CF₃-C₆H₄- | 136 |
| 40 | C₂H₅ | H | C₆H₅ | CF₃-C₆H₄- | 128 |
| 41 | C₂H₅ | CH₃ | CH₃ | Cl-C₆H₄- | 96 |
| 42 | C₂H₅ | CH₃ | CH₃ | NO₂-C₆H₄- | 162 |
| 43 | C₂H₅ | H | C₆H₅ | Cl-C₆H₄- | 124 |
| 44 | C₂H₅ | H | C₆H₅ | NO₂-C₆H₄- | 192 |
| 45 | C₂H₅ | H | furyl | Cl-C₆H₄- | 101 |
| 46 | C₂H₅ | H | furyl | NO₂-C₆H₄- | 219 |
| 47 | C₃H₇-i | —(CH₂)₅— | | C₄H₉-t | 65-7 |
| 48 | C₃H₇-i | H | C₃H₇-i | C₄H₉-t | 83-4 |
| 49 | C₃H₇-i | H | C₆H₅ | C₄H₉-t | 74-5 |
| 50 | C₃H₇-i | H | furyl | C₄H₉-t | 124-8 |
| 51 | C₃H₇-i | H | Cl-C₆H₄- | C₄H₉-t | 117-20 |
| 52 | C₃H₇-i | H | cyclohexyl | C₄H₉-t | 111-13 |

Table 1-continued

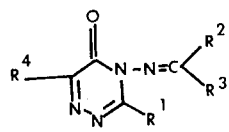

| Example No. | R¹ | R² | R³ | R⁴ | Melting point °C |
|---|---|---|---|---|---|
| 53 | $C_3H_7$-i | H | (thiophen-2-yl) | $C_4H_9$-t | 91 |

The active compounds according to the invention have excellent herbicidal properties and can therefore be used for combating weeds.

By weeds in the broadest sense there are understood all plants which grow in locations where they are undesired.

Weeds concerned are in paticular: dicotyledons, such as mustard (Sinapis), cress (Lepidium), cleavers (Galium) chickweed (Stellaria), camomile (Matricaria), gallant soldier (Galinsoga), goosefoot (Chenopodium), annual nettle (Urtica), knot grass (Polygonum), groundsel (Senecio), and rough-haired amaranth (Amaranthus retroflexus); monocotyledons such as timothy (Phleum), bluegrass (Poa), fescue (Festuca), goosegrass (Eleusine), panic grass (Setaria), ryegrass (Lolium), cheat (Bromus), barnyard grass (Echinochloa), wild oat (Avena fatua), foxtail grass (Alopecurus) and sorghum (Sorghum halepense).

Because of their very good toleration by best plants, the active compounds according to the invention are preferably suitable for selective combating of weeds in beet. Furthermore they can be used very successfully for the selective combating of weeds in oats, wheat, cotton, maize, tomatoe, potatoe, and soybean.

The active componds according to the present invention can be converted into the usual formulations, such as solutions, emulsions, suspensions, powders, pastes and granulates. These may be produced in known manner, for example by mixing the active compounds with extenders, that is, liquid or solid or liquid or solid or liquefied gaseous diluents or carriers, optionally with the use of surface-active agents, that is, emulsifying agents and/or dispersing agents, and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or atrongly polar solvents, such as dimethyl formamide, dimethyl sulphoxide or acetonitrile, as well as water.

By liquefied gaseous diluents or carriers are meant liquids which would be gaseous at normal temperatures and pressures, e.g., aerosol propellants, such as halogenated hydrocarbons, e.g., freon.

As solid diluents or carriers, there are preferably used ground natural minerals, such as kaolins, clays, talc, chalk, quartz, attapulgite, montmorillonite or diatomaceous earth, or ground synthetic minerals, such as highlydispersed silicic acid, alumina or silicates.

Preferred examples of emulsifying and foam-forming agents include non-ionic and anionic emulsifiers, such as polyoxyethylene-fatty acid esters, polyoxyethylenefatty alcohol ethers, for example alkylarylpolyglycol ethers, alkyl sulphonates, alkyl sulphates and aryl sulphonates as well as albumin hydrolyzation products; and preferred examples of dispersing agents include lignin, sulphite waste liquors and methyl cellulose.

The active compounds according to the invention can be used as mixtures with other active compounds.

The formulations in general contain from 0.1 to 95 percent by weight of active compound, preferably 0.5 to 90 percent by weight.

The active compounds can be used as such or in the form of their formulations or the use forms prepared therefrom, such as ready-to-use solutions, emulsifiable concentrates, emulsions, suspensions, spraying powders, pastes, soluble powders, dusting agents and granules. They may be applied in the customary manner, for example by squirting, spraying, atomizing, dusting, sprinkling, fumigating, gassing, watering, dressing or encrusting.

The compositions may be diluted for actual application, and the active compound concentrations in the ready-to-use preparations can be varied within wide ranges. In general they are from 0.0001 to 10%, preferably 0.01 to 1% by weight.

The active compounds can also be used with good success in the ultra-low volume method (ULV), where it is possible to apply formulations of up to 95% strength or even the 100% strength active compound alone.

The active compounds according to the invention can be used both in the pre-emergence and in the post-emergence method. They are particularly active in the post-emergence method and in this use form they are distinguished by particularly great toleration by beet.

The amount of active compound employed can be varied within wide ranges. It depends generally on the nature of the desired effect. In general, the amounts applied are from 0.1 to 25 kg/ha, preferably 0.3 to 8 kg/ha, of the area of crop cultivation.

The invention therefore provides a herbicidal composition containing as active ingredient a compound according to the invention in admixture with a solid or liquefied gaseous diluent of carrier or in admixture with a liquid diluent or carrier containing a surface-active agent.

The invention also provides a method of combating weeds which comprises applying to the weeds or their habitat a compound according to the invention alone or in the form of a composition containing as active ingredient a compound according to the invention in admixture with a diluent or carrier.

The invention also provides means of growing crops protected from damage by weeds by being grown in areas in which, immediately prior to and/or during the time of the growing, a compound according to the invention was applied alone or in admixture with a diluent or carrier. It will be seen that the usual methods of providing a harvested crop may be improved by the present invention.

The compounds according to the invention, and the preparation and use of the compounds according to the invention, are illustrated by the following Examples.

EXAMPLE A

Pre-emergence test

Solvent: 5 parts by weight of acetone
Emulsifier: 1 part by weight of alkylarylpolyglycol ether To produce a suitable preparation of active compound, 1 part by weight of active compound was mixed with the stated amount of solvent, the stated amount of emulsifier was added and the concentrate was then diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the test plants was determined and characterized by the values 0 – 5, which had the following meaning:

0 no effect
  1 slight damage or delay in growth
  2 marked damage or inhibition of growth
  3 heavy damage and only deficient development or only 50% emerged
  4 plants partially destroyed after germination or only 25% emerged
  5 plants completely dead or not emerged.

The active compounds, the amounts applied and the results obtained can be seen from Tables $A^1$ and $A^2$.

Table $A^1$

| Active compound | pre-emergence test Amount used kg/ha | Beet | Galinsoga | Matricaria | Stellaria | Urtica | Poa |
|---|---|---|---|---|---|---|---|
| 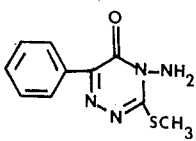 (known) | 5<br>2.5 | 5<br>5 | 5<br>5 | 5<br>5 | 5<br>4 | 5<br>5 | 5<br>4 |
| 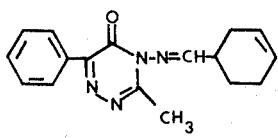 | 5<br>2.5 | 0<br>0 | 4–5<br>4–5 | 5<br>5 | 5<br>5 | 5<br>5 | 4<br>4 |

Table $A^2$

| Active compound | pre-emergence test Amount used kg/ha | Oats | Wheat | Cotton | Maize | Chenopodium | Stellaria | Galinsoga | Matricaria | Lolium |
|---|---|---|---|---|---|---|---|---|---|---|
| 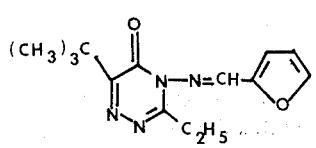 | 1.25<br>0.625<br>0.3125 | 3<br>2<br>1 | 2<br>1<br>0 | 2<br>1<br>0 | 2<br>2<br>1 | 5<br>4–5<br>4–5 | 5<br>5<br>5 | 5<br>5<br>5 | 5<br>5<br>5 | 5<br>5<br>5 |

Table A 2-continued

| Active compound | Amount used kg/ha | pre-emergence test | | | | | | | | |
|---|---|---|---|---|---|---|---|---|---|---|
| | | Oats | Wheat | Cotton | Maize | Cheno-podium | Stellaria | Galin-soga | Matri-caria | Lol-ium |
| 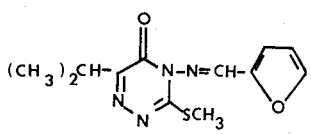 (known) | 1.25 | 5 | 4 | 4–5 | 4 | 5 | 5 | 5 | 4–5 | 5 |
| | 0.625 | 4–5 | 4 | 4 | 3 | 4 | 5 | 5 | 3 | 4 |
| | 0.3125 | 3 | 3 | 4 | 2 | 4 | 4 | 4 | 3 | 3 |

EXAMPLE B

Post-emergence test

Solvent: 5 parts by weight of acetone
Emulsifier: 1 part by weight of alkylaryl polyglycol ether.

To produce a suitable preparation of active compound, 1 part by weight of active compound was mixed with the stated amount of solvent, the stated amount of emulsifier was added and the concentrate was then diluted with water to the desired concentration.

Test plants which had a height of about 5 – 15 cm were sprayed with the preparation of the active compound in such a way that the amounts of active compound per unit area shown in the table were applied. Depending on the concentration of the spraying liquor, the amount of water used was between 1,000 and 2,000 liters per hectare. After three weeks, the degree of damage to the plants was determined and characterized by the values 0 – 5, which had the following meaning:

0 no effect
1 a few slightly burnt spots
2 marked damage to leaves
3 some leaves and parts of stalks partially dead
4 plant partially destroyed
5 plant completely dead The active compounds, their concentrations and the results obtained can be seen from Table B.

Table B

| Active compound | Amount used kg/ha | Post-emergence test | | | | | | | | |
|---|---|---|---|---|---|---|---|---|---|---|
| | | Beet | Avena fatua | Echino-chloa | Alopec-ures myo-suroides | Poa | Sorghum hale-pense | Poly-gonum | Amar-anthus | Urtica |
| 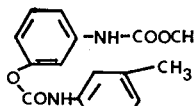 (known) | 4 | 0 | 3 | 4 | 4 | 3 | 4–5 | 5 | 3 | 5 |
| | 2 | 0 | 2 | 4 | 4 | 3 | 4–5 | 5 | 4 | 5 |
| | 1 | 0 | 1–2 | 3 | 3 | 2 | 4–5 | 4–5 | 3 | 3 |
| 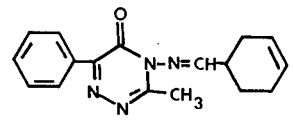 | 4 | 0 | 4 | 4–5 | 4–5 | 5 | 5 | 5 | 5 | 5 |
| | 2 | 0 | 3–4 | 4–5 | 4 | 4–5 | 5 | 5 | 5 | 5 |
| 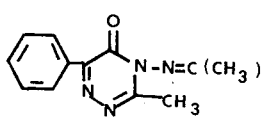 | 4 | 1 | 4–5 | 3–4 | 4 | 4–5 | 5 | 4 | 5 | 5 |
| | 2 | 0 | 4 | 2–3 | 4 | 4–5 | 5 | 3–4 | 5 | 4 |
| 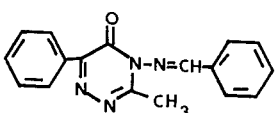 | 4 | 1–2 | 4 | 4 | 4 | 4 | 5 | 3 | 5 | 4–5 |
| | 2 | 1 | 3–4 | 3–4 | 4 | 3–4 | 5 | 1–2 | 4–5 | 4 |

It will be understood that the specification and examples are illustrative but not limitative of the present invention and that other embodiments within the spirit and scope of the invention will suggest themselves to those skilled in the art.

What is claimed is:

1. Azomethine compound of 4-amino-5-H-1,2,4-triazine-5-one of the formula

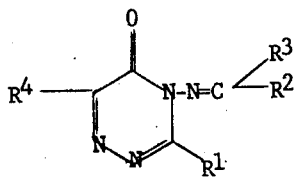

in which:
R¹ is alkyl of up to 20 carbon atoms, cycloalkyl of 3 to 6 carbon atoms or phenyl,
R² is hydrogen or alkyl of up to 4 carbon atoms,
R³ is alkyl or alkoxy of up to 4 carbon atoms, cycloalkyl or cycloalkenyl of 5 to 7 carbon atoms, aralkyl with 6 to 10 carbon atoms in the aryl moiety and 1 or 2 carbon atoms in the alkyl moiety, aryl or aryl substituted with alkyl with up to 3 carbon atoms, chlorine, nitro or trifluoromethyl; or furyl, thienyl or pyrryl or R³ is dialkylamino wherein each alkyl moiety, independently of the other, contains 1 to 4 carbon atoms, or represents furyl or thienyl or
R² and R³ jointly represent an alkylene bridge of 2 to 6 carbon atoms which can be interrupted by oxygen, sulfur, or NH and
R⁴ represents alkyl with up to 4 carbon atoms, phenyl or substituted phenyl substituted once or twice by halogen, straight-chain or branched alkyl with 1 to 4 carbon atoms, halomethyl with 1 to 3 halogen atoms, alkoxy or alkylthio with 1 to 4 carbon atoms, sulfonylalkyl, or nitro.

2. Azomethine compound as claimed in claim 1, wherein R¹ is alkyl of 1 to 15 carbon atoms.

3. Azomethine compound as claimed in claim 1, wherein R¹ is cycloalkyl of 3 to 6 carbon atoms.

4. Azomethine compound as claimed in claim 1, wherein R¹ is phenyl.

5. Azomethine compound as claimed in claim 1, wherein R² is hydrogen.

6. Azomethine compound as claimed in claim 1, wherein R² is alkyl of up to 4 carbon atoms.

7. Azomethine compound as claimed in claim 1, wherein R³ is alkyl or alkoxy of up to 4 carbon atoms.

8. Azomethine compound as claimed in claim 1, wherein R³ is cycloalkyl or cycloalkenyl of 5 to 7 ring carbon atoms.

9. Azomethine compound as claimed in claim 1, wherein R³ is aralkyl of 6 to 10 carbon atoms in the aryl moiety, and 1 or 2 carbon atoms in the alkyl moiety.

10. Azomethine compound as claimed in claim 1, wherein R³ is furyl, thienyl, or pyrryl.

11. Azomethine compound as claimed in claim 1, wherein R³ is dialkylamino wherein each alkyl moiety is of from 1 to 4 carbon atoms.

12. Azomethine compound as claimed in claim 11, wherein said alkyl moieties form a heterocyclic ring containing from 2 to 5 ring carbon atoms, which ring may also contain oxygen, sulfur or an NH group.

13. Azomethine compound as claimed in claim 1, wherein R³ is substituted aryl wherein the substituent is at least one of alkyl of up to 3 carbon atoms, halogen, nitro and haloalkyl.

14. Azomethine compound as claimed in claim 1, wherein R² and R³ jointly represent an alkylene bridge of from 2 to 6 carbon atoms, which bridge may be interrupted by a hetero atom selected from oxygen, sulfur or an NH moiety.

15. Azomethine compound as claimed in claim 1, designated 3-methyl-4-benzylideneamino-6-phenyl-5-H-1,2,4-triazin-5-one.

16. Azomethine compound as claimed in claim 1, designated 3-ethyl-4-benzylideneamino-6-tert.butyl-5-H-1,2,4-triazin-5-one.

17. Azomethine compound as claimed in claim 1, designated 3-methyl-4-(1',2',3',6'-tetrahydro-benzylideneamino)-6-phenyl-5-H-1,2,4-triazin-5-one.

18. Azomethine compound as claimed in claim 1, designated 3-ethyl-4-isopropylideneamino-6-(3'-trifluoromethylphenyl)-5-H-1,2,4-triazin-5-one.

19. Azomethine compound as claimed in claim 1, designated 3-ethyl-4- isopropylideneamino-6-(3'-chlorophenyl)-5-H-1,2,4-triazin-5-one.

20. Azomethine compound as claimed in claim 1, designated 3-ethyl-4-benzylideneamino-6-(3'-chlorophenyl)-5-H-1,2,4-triazin-5-one.

21. Azomethine compound as claimed in claim 1, designated 3-isopropyl-4-isopropylideneamino-6-tert.butyl-5-H-1,2,4-triazin-5-one.

22. Azomethine compound as claimed in claim 1, designated 3-isoproyl-4-isobutylideneamino-6-tert.butyl-5-H-1,2,4-triazin-5-one.

23. Azomethine compound as claimed in claim 1, designated 3-isopropyl-4-benzylideneamino-6-tert.butyl-5-H-1,2,4-triazin-5-one.

24. Azomethine compound as claimed in claim 1, designated 3-isopropyl-4-(4'-chloro-benzylideneamino)-6-tert.butyl-5-H-1,2,4-triazin-5-one.

25. Azomethine compound as claimed in claim 1, designated 3-isopropyl-4-hexahydrobenzylideneamino-6-tert.butyl-5-H-1,2,4-triazin-5-one.

26. Azomethine compound as claimed in claim 1, designated 3-isopropyl-4-furfurylideneamino-6-tert.butyl-5-H-1,2,4-triazin-5-one.

* * * * *